(12) United States Patent
Jia

(10) Patent No.: US 8,099,967 B2
(45) Date of Patent: Jan. 24, 2012

(54) PORTABLE RACK CARRIER DEVICE AND THE METHOD OF USE

(76) Inventor: Yu Jia, Houston, TX (US)

( * ) Notice: Subject to any disclaimer, the term of this patent is extended or adjusted under 35 U.S.C. 154(b) by 643 days.

(21) Appl. No.: 12/329,954

(22) Filed: Dec. 8, 2008

(65) Prior Publication Data

US 2009/0255288 A1    Oct. 15, 2009

Related U.S. Application Data

(60) Provisional application No. 61/123,589, filed on Apr. 10, 2008, provisional application No. 61/137,314, filed on Jul. 30, 2008.

(51) Int. Cl.
*F25D 17/02* (2006.01)
(52) U.S. Cl. ............................................. 62/64; 62/266
(58) Field of Classification Search .............. 62/64, 266, 62/336, 374, 378; 414/331.04, 331.13
See application file for complete search history.

(56) References Cited

U.S. PATENT DOCUMENTS

| | | | | |
|---|---|---|---|---|
| 4,300,356 A * | 11/1981 | Notaro et al. | .................. | 62/48.1 |
| 4,459,825 A * | 7/1984 | Crouch | ........................... | 62/404 |
| 4,485,641 A * | 12/1984 | Angelier et al. | ............... | 62/51.1 |
| 4,665,713 A * | 5/1987 | Delatte | ......................... | 62/382 |
| 4,899,968 A * | 2/1990 | Eaglin et al. | .................. | 248/131 |
| 5,230,439 A * | 7/1993 | Klok et al. | .................. | 73/304 C |
| 5,309,722 A * | 5/1994 | Phillips, Jr. | .................... | 62/49.1 |
| 5,355,684 A * | 10/1994 | Guice | ........................... | 62/54.2 |
| 5,620,110 A * | 4/1997 | Delatte | ....................... | 220/560.1 |
| 5,898,105 A * | 4/1999 | Owens | ......................... | 73/49.8 |
| 6,226,997 B1* | 5/2001 | Vago | .............................. | 62/130 |
| 6,505,547 B1* | 1/2003 | Burnett et al. | .................. | 99/494 |
| 7,428,873 B1* | 9/2008 | Searle et al. | ..................... | 109/24 |
| 7,905,502 B2* | 3/2011 | Oliver | ......................... | 280/47.18 |
| 2006/0010881 A1* | 1/2006 | Gustafson | ...................... | 62/47.1 |
| 2006/0260328 A1* | 11/2006 | Rampersad | ......................... | 62/6 |
| 2008/0042060 A1* | 2/2008 | Nakasuji et al. | ............... | 250/310 |
| 2008/0206807 A1* | 8/2008 | Duymelinck et al. | ........ | 435/40.5 |

* cited by examiner

*Primary Examiner* — Mohammad Ali

(57) ABSTRACT

A unique device for facilitating insertion and retrieval of biological specimens into and from a liquid nitrogen storage tank and a method of using the device is disclosed. The device basically has one U-shaped mainframe body, two handles, one semi-circular switch, four hooks, one rack rod locker, and one cross-shaped sample box holder.

8 Claims, 4 Drawing Sheets

PORTABLE RACK CARRIER DEVICE AND THE METHOD OF USE

REFERENCE TO RELATED APPLICATIONS

This application claims the benefit of the filing date of U.S. Provisional Application Ser. No. 61/123,589, entitled "Method and device for facilitating insertion and retrieval of biological specimens in liquid nitrogen storage tanks" and filed on Apr. 10, 2008, and the benefit of the filing date of U.S. Provisional Application Ser. No. 61/137,314, entitled "Method and device for facilitating insertion and retrieval of samples in cryogenic storage tanks" and filed on Jul. 30, 2008. The teachings of the entire referenced applications are incorporated herein by reference.

FIELD OF THE INVENTION

The present invention relates generally to an accessory of a cryogenic storage tank. More particularly, this invention relates to an associated device or apparatus for facilitating insertion and retrieval of biological specimens into and from a liquid nitrogen storage tank and a method of using the device.

BACKGROUND OF THE INVENTION

Many types of cryogenic storage units exist for various scientific or industrial purposes. These units rely on methods of refrigeration that allow items to be cooled often below $-100°$ C. For some of coldest storage applications, liquid cryogen, such as nitrogen, is contained within a tank and the items to be stored or otherwise treated are simply immersed in this bath of liquid cryogen.

There are many previously known cryogenic storage tanks which are generally cylindrical in shape and have a closed bottom and open top thus defining a cryogenic freezing chamber. Normally, the open top has a dimension of 3 to 5¾ inches. A source of liquefied gaseous material, typically liquid nitrogen, is fluidly connected to the interior of the chamber through a valve system so that the liquid level within the cryogenic chamber is maintained within predetermined limits. A lid is also conventionally disposed across the open top of the cryogenic tank.

In use, frozen biological specimens contained in tubes or boxes, such as blood, semen or other types of biological specimens including bacteria, virus, yeast, parasite, and mammalian cells, are simply immersed in the liquid contained within the cryogenic chamber thus storing the biological materials in the desired fashion. Since the temperature of the liquefied gaseous material is extremely low, e.g. below $-191°$ C., the viability of the biological specimens can be maintained for long periods of time.

However, it is normally not easy to move or handle these specimens-containing boxes in a removable rack out of the liquid nitrogen tanks. Necessarily, it needs at least two people or lab technicians to hold the stick of racks which containing such boxes (one operator) and look for samples within different boxes at the same time (another operator). It is not unusual to see samples and/or liquid nitrogen falling on the ground or samples falling into the liquid nitrogen tank if there is only one person handling the situation. On the other hand, if there is only one person, that person will take out the rack, put it on the ground, then take out the boxes from the rack and look for their wanted samples in the boxes. This will leave the frozen biological specimens outside the liquid nitrogen tank and at the room temperature for a while, frequently decreases the viability of the refrozen biological specimens. If the samples fall into the liquid nitrogen from the rack as mentioned above, cross contamination between the biological specimens is possible and any impurities, diseases, viruses or the like contained within that biological specimen may be transmitted to a different biological specimen also contained within the same cryogenic freezing tank.

The present invention is to provide a portable device, designed as a liquid nitrogen accessory, applicable to majority of conventional liquid nitrogen tanks. This invention provides a unique device which overcomes all of the above mentioned disadvantages in handling samples from liquid nitrogen tanks. Currently, there is neither any similar device/apparatus in the market nor any prior art found for the same purpose after comprehensive search.

SUMMARY OF THE INVENTION

For scientific purposes, cryogenic storage tanks are generally used for storage of biological specimens, including human tissue and cell lines. The most generally used conventional cryogenic storage units are simple liquid nitrogen containers with removable racks having multiple shelves. Specimens are inserted and removed from the storage tanks manually through a door at the top of the tank. When a specimen needs to be inserted or retrieved into and from a liquid nitrogen storage tank, the specific rack, in which the specimen is located or will be located, needs to be completely taken out of the storage tank, which usually results in following problems. First of all, during this process, the whole rack usually has to be set outside the tank long enough to let the specimens expose to thawing temperature, with a resultant decrease in the viability of the refrozen biological specimens; Secondly, taking out the rack usually brings out some liquid nitrogen that may damage the materials exposed to the liquid nitrogen like floor, and even worse, spill out and harm the operators; last but not least, this inconvenient process with multiple steps usually needs more than one operator to be involved. Therefore, it would be advantageous if a method and device could be conceived to resolve these particular problems.

A novel and unique device (here called "Rack Carrier") designed for a liquid nitrogen tank accessory, in accordance with the present invention, is a stainless steel frame structure, basically having one U-shaped mainframe body, two handles, one semi-circular switch, four hooks, one rack rod locker, and one cross-shaped sample box holder.

One operator can hold the above two handles with both of his/her hands and put the called Rack Carrier on the top of the liquid nitrogen tank by setting the above four hooks on the edge of the neck of the liquid nitrogen tank. Then, after setting the semi-circular switch at a flat position ready to hold the rack, without any blocking, smoothly pull a rack out of the liquid nitrogen tank by holding the stick of the rack and set the rack in the Rack Carrier at the level desired since the two tips in such semi-circular switch will automatically hold the rack at one side of the rack when the operator releases the rack at his/her desired position. Further, take out or unlock the rack rod from the rack and put it into the rack rod locker. Finally, take out the boxes from the same rack and look for the samples wanted. After finding the wanted samples, the operator can hold the stick of the rack and, at the same time, push down on the semi-circular handle resulting in the two tips of such semi-circular switch turning up to a position to release the rack from the Rack Carrier so the operator can remove the rack from the Rack Carrier. Then the rack can be put back into the liquid nitrogen tank to its original location. By this way, the specimens are maintained at a substantially constant low temperature during the operation since the rack is kept at the entrance of the tank where the temperature is almost identical with that inside the tank. This prevents the specimens from exposing to the thawing temperatures and minimizes the decrease in the viability of the biological specimens. Also, damages to the operators and to the materials around the liquid nitrogen tank, like floor, will be avoided or minimized. In addition, the Rack Carrier was designed to be a simple structure without using any sort of electrical power, computer systems, or programs, so it is easy to be manufactured and easy to learn how to use and maintain or repair it with less frequency to malfunction or breakdown. Furthermore, only one operator is needed to handle this device. The operator can finish fetching samples from liquid nitrogen tanks all by him/her self without any catastrophic consequences.

In summary, the present invention provides an applicable method and a simple, handy, novel, and inexpensive device to facilitate insertion and retrieval of biological specimens within a liquid nitrogen storage tank. The method of fetching samples from liquid nitrogen tanks by using the above Rack Carrier device is made simple, quick, safe, convenient, and economic. This invention also solves many persistent problems when people handle samples from liquid nitrogen storage tanks.

A better understanding of the present invention will be had upon reference to the following detailed description when read in conjunction with the accompanying drawings.

DETAILED DESCRIPTION OF THE PREFERRED EMBODIMENTS

The preferred embodiments may be understood by referring to FIG. 1-4, which depict perspective views of the rack, the Rack Carrier, the semi-circular switch, and the interactions of the Rack Carrier with, the rack, and the liquid nitrogen storage tank.

Figure 1:
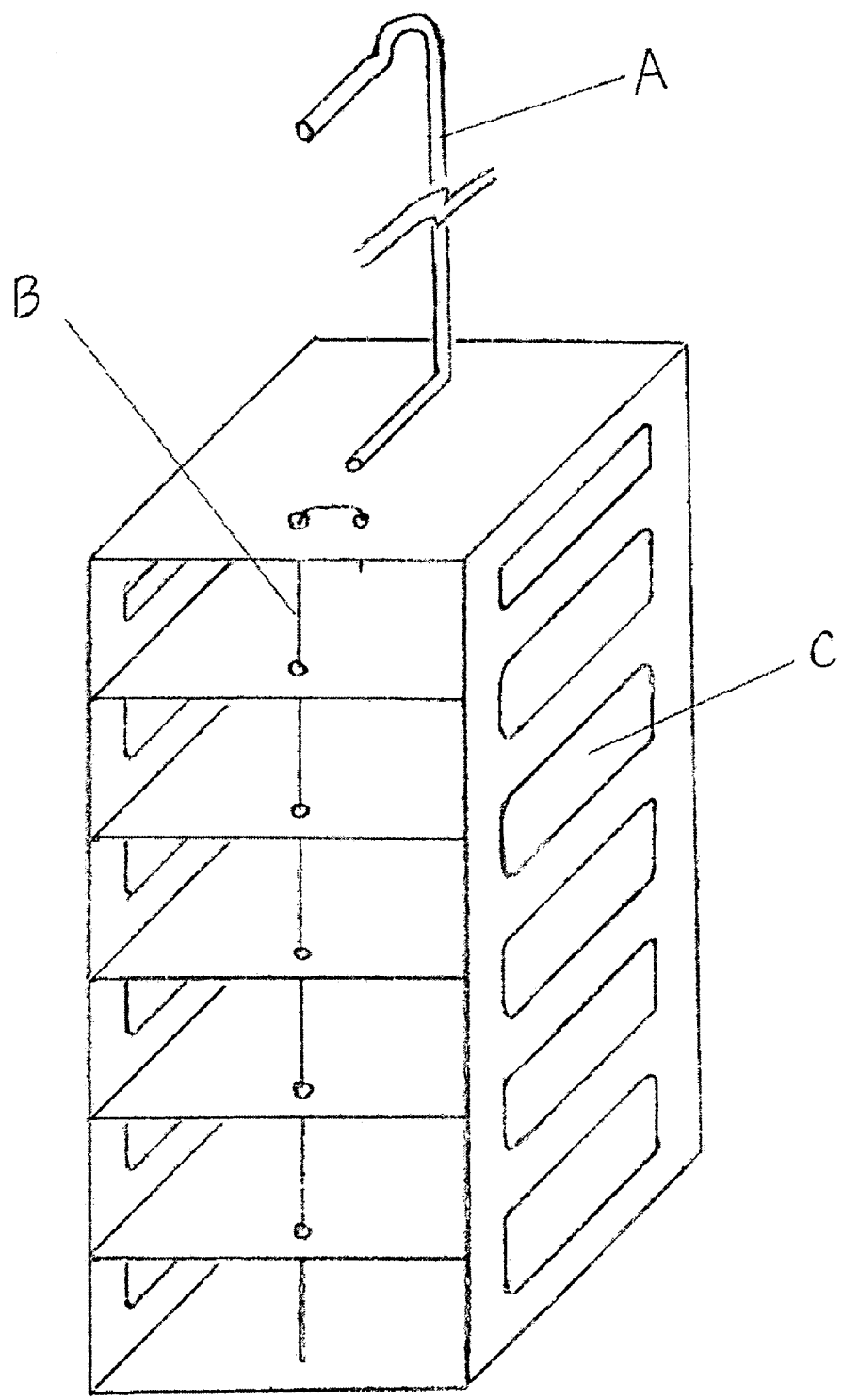
FIG. 1 presents a perspective view of a regular rack used in the liquid nitrogen storage tank.

In the drawing of FIG. 1, the said rack has been used as a sample storage device in liquid nitrogen storage tanks, also called cryogenic storage racks or freezer racks. Normally, a rack has box shape with one side open for removal or insertion of sample boxes. The size of the regular rack varies with 3×3×2, 5¼×5¼×1⅞, 5¼×5¼×2, 5¼×5¼×3, 5¼×5¼×3, and 5¾×5¾×1⅞ inches. There is a stick A attached on the rack for holding purpose and there is a rack rod B locked in the middle of the edge in the opening side to block the inside sample boxes out of the rack. More importantly, there are slots C on two opposite sides of the rack. Usually, the number of such slots is equal to the number of shelves in the rack and each shelf will hold one sample box. In this invention, the slot C of one side of the rack is used to stop the rack movement, into which the tips (7 and 7') of the semi-circular switch are inserted.

Figure 2:
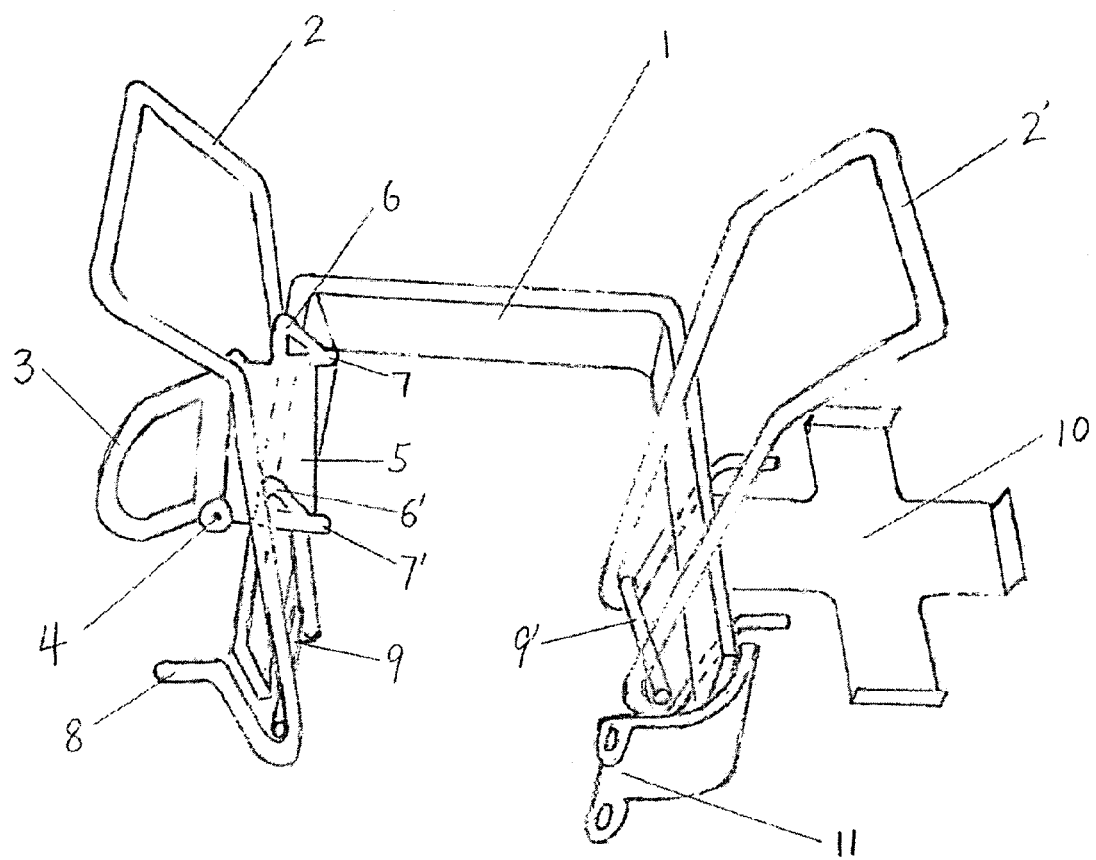
FIG. 2 presents a perspective view of the Rack Carrier.

In the drawing of FIG. 2, the said Rack Carrier comprises one U-shaped mainframe body 1, two Rack Carrier handles 2 and 2' on both sides, one semi-circular switch (including a semi-circular handle 3, an axis 4, a rectangular plate 5 within which there are two triangle-shaped stoppers 6 and 6' from which there are two tips 7 and 7' extrude outside of such two triangle-shaped stoppers), four tank neck edge hooks 8, two beams 9 and 9' fixed to the bottom of the Rack Carrier handle 2 and 2', one cross-shaped sample box Carrier 10, and one rack rod locker 11.

The mainframe body 1 is like a U-shaped or C-shaped construction, which has three sides with one side open to allow insertion and retrieval of specimens. The three sides are constructed with horizontal beams. Among the three side frames, two side frames attached with two identical structures in parallel with two handles on each side (opposite to each other), are named Rack Carrier handles 2 and 2'. Between the said two side frames, there is an open space for a rack. The size of the open space within the three side frames could be designed to suit any rack with any regular size for perfectly holding the rack without much space between the Rack Carrier and the rack. One of the said two side frames with Rack Carrier handles fixed to a semi-circular switch (3, 4, 5, 6, 6', 7 and 7') by any conventional way in the art, another of the said two side frames fixed to a cross-shaped sample box holder 10 by any conventional way in the art, both the semi-circular switch and the cross-shaped sample box holder can be switched for the convenience of right-handed or left-handed operators.

The Rack Carrier handles 2 and 2' were made from a single stainless steel stick that was bended at both ends to form the said tank neck edge hook 8. Both the Rack Carrier handles 2 and 2' are fixed to mainframe body 1 on two sides by any conventional way in the art. There are two small beams 9 and 9' sticking out at the bottom of the Rack Carrier handles 2 and 2' to stabilize the handle and let the Rack Carrier stand very steadily at the entrance of the tank while the bottom part of the Rack Carrier is inserted into the door of the tank.

The semi-circular switch includes a semi-circular handle 3 used to pull or push in order to hold a rack at some position or release a rack back to the liquid nitrogen tank, an axis 4 used to help the movement of the semi-circular switch, and a rectangular plate 5 within which there are two triangle-shaped stoppers 6 and 6' with two tips 7 and 7' extrude outside of such two triangle-shaped stoppers. A rack can be stopped at any level of shelves in a rack. The said two tips 7 and 7' above are the key parts used to stop the movement of a rack and used to hold the rack in a stable position by inserting into a slot of the rack. The two triangle-shaped stoppers 6 and 6' were used to smoothly stop the rack by letting the rack slide down gently to the two tips 7 and 7' along two triangle sides of the two triangle-shaped stoppers 6 and 6'.

The cross-shaped sample box holder 10, designed to hold any regular box used to store samples in a rack, was fixed to the mainframe body 1 at the opposite side of the semi-circular switch. This convenient box holder platform will allow an operator put the sample box very feasible and close to the top of the liquid nitrogen tank where it is very cold, not on the ground or any other place where it is far away from the liquid nitrogen tank.

The rack rod locker 11 is designed to hold a rod that is used in a regular rack, for preventing boxes inside from falling out of the rack. When an operator pulls out of a rack from a tank and sets it in the Rack Carrier, he or she would take out or unlock the rod from the rack and put it into the two holes of the rack rod locker 11. This rack rod locker 11 would keep the rod in a safety place and help prevent the boxes from falling out of the rack when the operator looks for samples in the box.

The whole Rack Carrier could be made from stainless steel or other metal materials that would make the Rack Carrier strong and last long. The Rack Carrier could also be designed comprising a stainless steel cube housing, having two completely closed sidewalls in parallel and other two sidewalls which are in parallel with opening windows, one of which has a big window to allow insertion and retrieval of specimens from at least 3 boxes in the rack simultaneously, and another of which has multiple small windows to prevent the specimens from falling out of the rack. All other parts are similar to the embodiments mentioned above.

Figure 3:
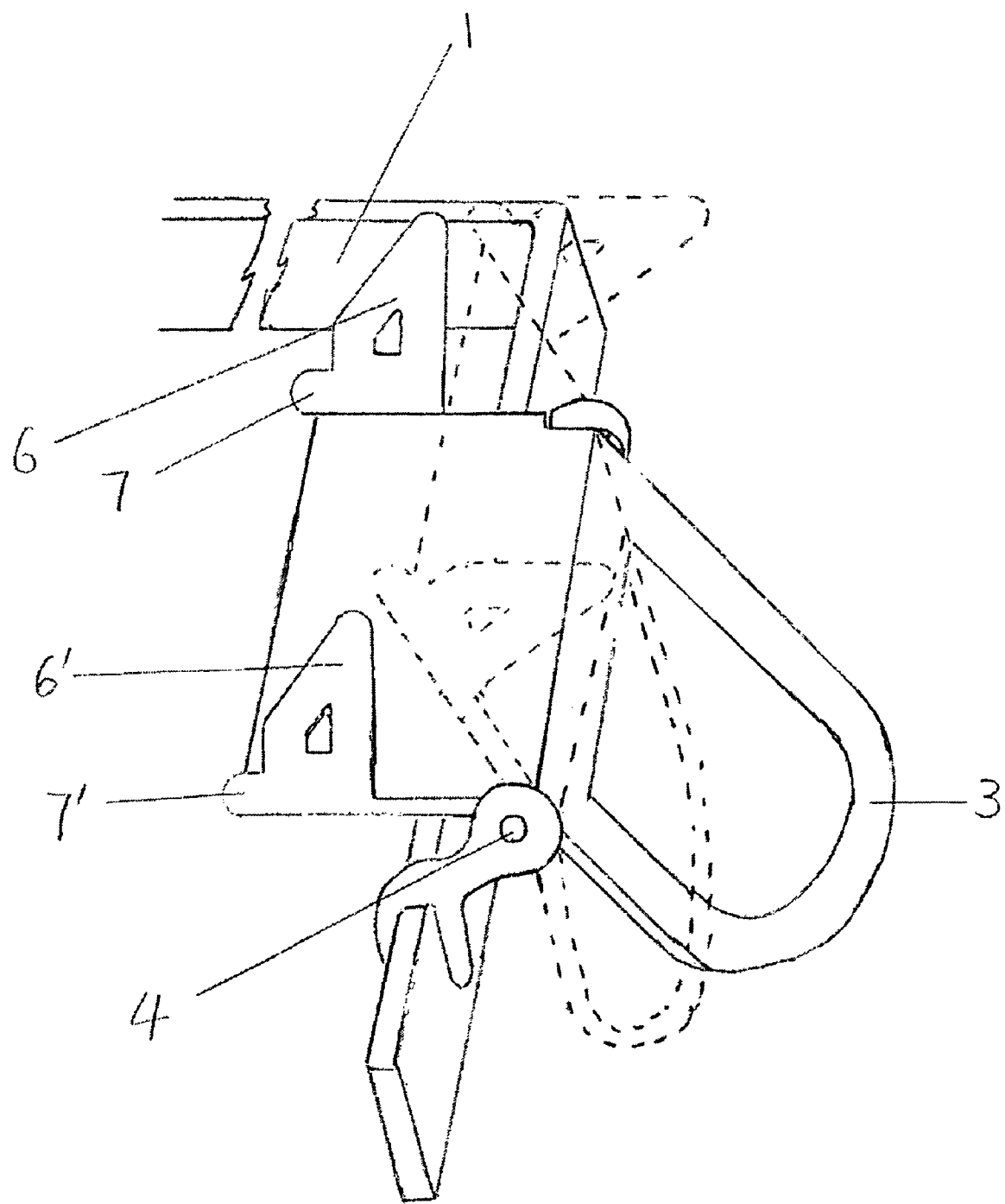
FIG. 3 presents a perspective view of the enlarged semi-circular switch of the Rack Carrier and its movement.

In the drawing of FIG. 3, except the above parts described in FIG. 2, the said semi-circular switch comprises a semi-circular handle 3 used to pull or push in order to hold a rack at some position or release a rack back to a liquid nitrogen tank, an axis 4 used to help the movement of the semi-circular switch, and a rectangular plate 5 within which there are two triangular-shaped stoppers 6 and 6' with two tips 7 and 7' extrude outside of such two triangular-shaped stoppers. The said two tips 7 and 7' above are the key parts used to stop the movement of a rack and used to hold the rack in a stable position. The two triangular-shaped stoppers 6 and 6' were used to smoothly stop the rack by letting the rack slide down gently to the two tips 7 and 7' along two triangle sides of the two triangular-shaped stoppers. Basically, a rack can be stopped at any level. During the process of pulling out a rack from a liquid nitrogen tank, the plate 5, triangular-shaped stoppers (6 and 6'), and the two tips (7 and 7') will be pushed up by the rack since there is an axis helping this movement and there is not much space between the plate 5 (including stoppers and tips) and the side of the rack, at the same time the semi-circular handle 3 will be downward or toward south following the turning up of the plate 5 (including stoppers and tips) as showed with dash lines in FIG. 3. When the operator finds the desired box in the rack and releases the rack, the rack will be stopped by letting the two stoppers (6 and 6') and the two tips (7 and 7') get into the nearest slot in the rack. The rack will be held tightly on the two tips (7 and 7'). At this moment the plate 5 and the two tips (7 and 7') will be at a flat level and the semi-circular handle 3 will be in an open position or toward west as shown in the solid lines in FIG. 3. After finding the desired sample(s), the operator can hold the stick on the top of the rack and at the same time push down the semi-circular handle 3 resulting in those two tips (7 and 7') turning up to a position (as showed in dash lines in FIG. 3.) to release the rack from the Rack Carrier. Then, the rack can be put back into the liquid nitrogen tank to its original location.

Figure 4:
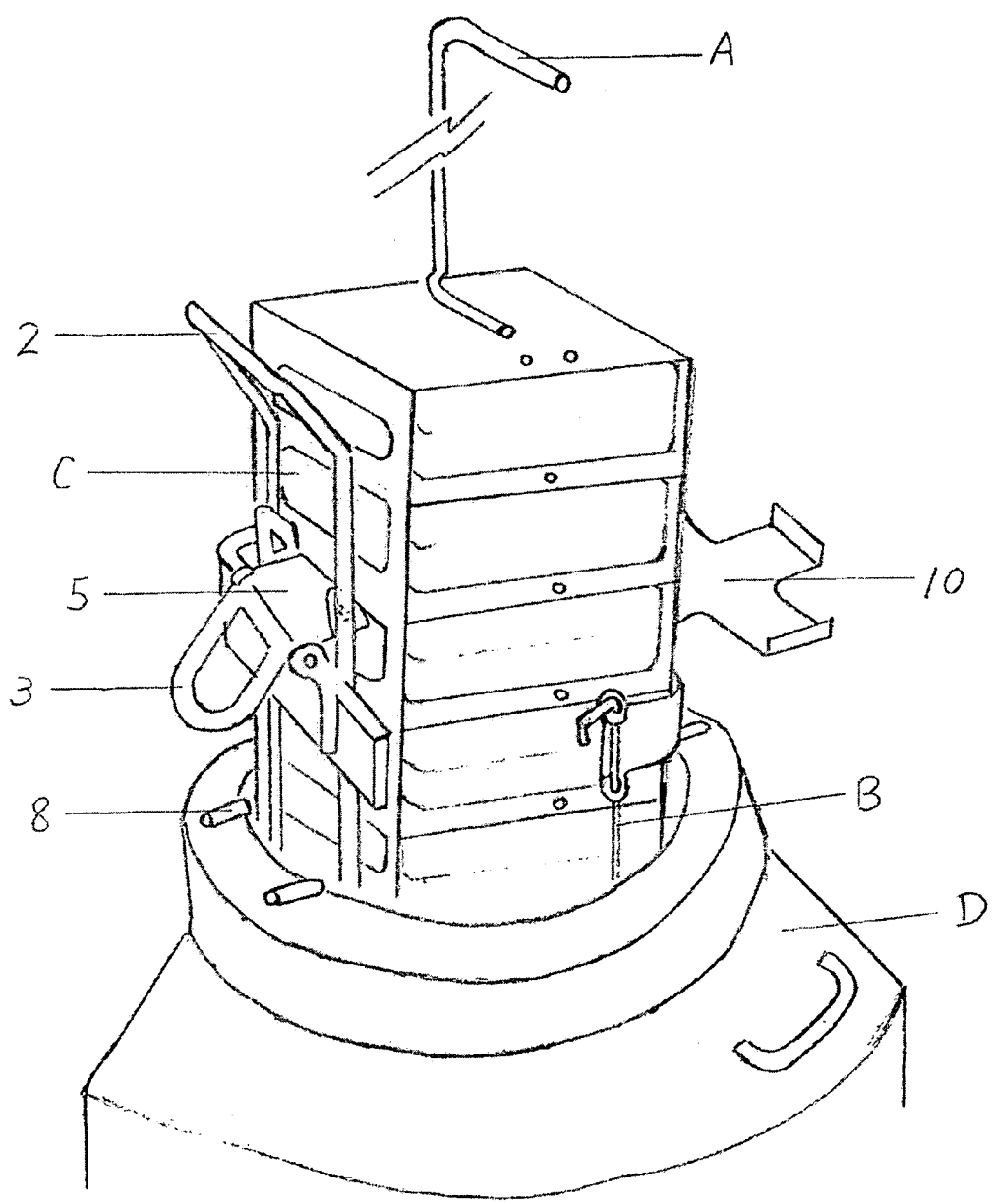
FIG. 4 presents a perspective view of a holding position of the Rack Carrier on the top of the liquid nitrogen storage tank.

FIG. 4 shows a rack is held in the Rack Carrier on the top of a liquid nitrogen tank D. In this drawing, the Rack Carrier's four tank neck edge hooks (8) are on the edge of the tank neck edge, which allows the Rack Carrier to stably sit on the top of the liquid nitrogen tank D. Also, the two tips (7 and 7') of the semi-circular switch are inside one side of the rack and hold the rack tightly, at the same time the plate 5 of the semi-circular switch is at the flat level and the semi-circular handle 3 is at the opening position or toward west.

This Rack Carrier is designed for letting the rack move upward without any resistance but be stopped from moving downward by the blade structure unless it is manually turned up to let the rack move downward to the tank. Whenever insertion or retrieval operation is needed, this stable device can stand at the entrance of the liquid nitrogen tank with the opening side facing the targeting specimen rack. Then the rack can be pulled up through the frame or cube structure until the target box appears at the appropriate level while the whole rack can be stopped by the semi-circular switch.

The advantage of the present invention is to provide a portable device, which has a simple construction and is easy to use and follow with no special care and maintenance. A more important purpose of the present invention is to provide a simple and quick but safe and convenient method and device, which will facilitate insertion and retrieval of biological specimens into and out of a liquid nitrogen storage tank. The device of the present invention could be manufactured inexpensively and is affordable to all laboratories and individuals. The present invention also provides such a method and/or apparatus, which will minimize the number of operators needed to be involved in the operation.

Although the rack carrier device and the method of using has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What is claimed is:

1. A rack carrier device for facilitating insertion and retrieval of biological specimens into and from a liquid nitrogen storage tank comprises: one U-shape mainframe body, two handles, one semi-circular switch, four hooks, one rack rod locker, and one cross-shaped sample box holder.

2. A rack carrier device of claim 1 is made from stainless steel or other metal materials.

3. A rack carrier device of claim 1, wherein said U-shaped mainframe body is constructed with three sides made from beams or sidewalls, wherein the size of the space within the above three sides is designed to fit any regular rack used in a liquid nitrogen tank.

4. A rack carrier device of claim 1, wherein said two handles are fixed to said mainframe body on two sides by any conventional way in the art, wherein there are two small beams fixed at the bottom of the said handles to stabilize the handles, wherein each said handle is made from one single stainless steel stick that was bended at both ends to form two hooks for sitting on the entrance of a liquid nitrogen tank.

5. A rack carrier device of claim 1, wherein the said one semi-circular switch is fixed to one side of the said mainframe body in claim 1 and includes a semi-circular handle, a rectangular plate, and an axis between and connecting the said semi-circular handle and the said rectangular plate, wherein the said rectangular plate has two triangle-shaped stoppers standing on two opposite sides of the said rectangular plate and toward a rack, wherein each said triangle-shaped stopper has a tip extruded toward a rack.

6. A rack carrier device of claim 1, wherein said one rack rod locker is fixed to the said mainframe body and is located on the opening side of the said U-shaped mainframe body and has two holes designed vertically to hold a rack rod.

7. A rack carrier device of claim 1, wherein said one cross-shaped sample box holder is fixed to the said mainframe body at the opposite side of said semi-circular switch and is designed to hold any regular sample box used in a rack.

8. A method of carrying a rack from and into a liquid nitrogen tank using a rack carrier device of claim 1, comprising the following steps:
  1) Put a rack carrier device of claim 1 on the entrance of a liquid nitrogen tank by letting the said four hooks of claim 1 sit on the edge of the tank neck;
  2) Pull out a rack from a liquid nitrogen tank by holding the stick on the top of the rack, within the space of the U-shaped mainframe body of claim 3;
  3) Release the above rack whenever finding a desired sample box in the rack;
  4) Unlock a rack rod from the rack and keep it into the rack rod locker of claim 6;

5) Take out the desired sample box, search for sample(s), and put back the sample box after finishing the insertion and/or retrieval of sample(s);
6) Put the rack rod back and lock it into the rack;
7) Hold the stick on the top of the rack with one hand and at the same time push down the semi-circular handle of claim 5 with another hand to release the rack from the rack carrier device of claim 1 and then put the rack back into the liquid nitrogen tank to its original location.

\* \* \* \* \*